United States Patent
McBeth et al.

(10) Patent No.: US 6,203,526 B1
(45) Date of Patent: Mar. 20, 2001

(54) APPARATUS FOR PREVENTING LOSS OF A COMPOSITION DURING A MEDICAL PROCEDURE

(75) Inventors: Dean M. McBeth, Croton-on-Hudson; Vincent DeCrescito, Malverne Park, both of NY (US); Richard Kronenthal, Fairlawn, NJ (US)

(73) Assignee: Direct Therapeutics, Inc., White Plains, NY (US)

( * ) Notice: Subject to any disclaimer, the term of this patent is extended or adjusted under 35 U.S.C. 154(b) by 0 days.

(21) Appl. No.: 09/138,025

(22) Filed: Aug. 21, 1998

Related U.S. Application Data (60) Provisional application No. 60/074,544, filed on Feb. 12, 1998, and provisional application No. 60/056,836, filed on Aug. 22, 1997.

(51) Int. Cl.[7] ............................ A61M 29/00; A61M 5/00
(52) U.S. Cl. ........................................ 604/96.01; 604/246
(58) Field of Search ..................................... 604/104, 105, 604/106, 107, 264, 280, 246, 96, 101, 96.01, 101.04, 99.04, 103.03

(56) References Cited

U.S. PATENT DOCUMENTS

| | | |
|---|---|---|
| 3,241,554 * | 3/1966 | Coanda . |
| 3,331,371 * | 7/1967 | Rocchi et al. . |
| 4,263,917 | 4/1981 | Moss .................................... 128/656 |
| 4,762,125 | 8/1988 | Leiman et al. .................. 128/207.15 |
| 4,802,885 | 2/1989 | Weeks et al. ........................... 604/93 |
| 4,850,349 | 7/1989 | Farahany ......................... 128/207.15 |
| 5,015,232 | 5/1991 | Maglinte ............................... 604/96 |
| 5,056,515 | 10/1991 | Abel ................................ 128/207.15 |
| 5,147,318 | 9/1992 | Hohn .................................... 604/174 |
| 5,151,087 | 9/1992 | Jonkman .............................. 604/164 |
| 5,197,948 * | 3/1993 | Ghodsian ............................... 604/30 |
| 5,286,254 | 2/1994 | Shapland et al. ....................... 604/21 |
| 5,308,325 * | 5/1994 | Quinn et al. ........................... 604/96 |
| 5,344,439 * | 9/1994 | Otten . |
| 5,429,609 | 7/1995 | Yoon ................................... 604/167 |
| 5,451,232 * | 9/1995 | Rhinehart et al. . |
| 5,454,790 | 10/1995 | Dubrul ................................ 604/104 |
| 5,599,317 | 2/1997 | Hauser ................................ 604/256 |
| 5,683,363 * | 11/1997 | McKeever ............................. 604/96 |
| 5,738,653 * | 4/1998 | Pinchuk et al. ........................ 604/96 |
| 5,743,875 * | 4/1998 | Sirhan et al. .......................... 604/96 |
| 5,833,650 * | 11/1998 | Imran ................................... 604/53 |

* cited by examiner

*Primary Examiner*—Sharon Kennedy
(74) *Attorney, Agent, or Firm*—Darby & Darby

(57) ABSTRACT

In a method and apparatus for delivering a composition to a targeted area of tissue, exposure of a non-targeted tissue to the composition is minimized. The apparatus has at least one needle-like shaft which is inserted through a track in the non-targeted tissue to deliver the composition to the targeted tissue through an opening in the shaft. The track may be a naturally occurring lumen in a tissue, such as a vascular lumen, or may be a track created surgically by a diagnostic instrument, or by the needle-like shaft of the present apparatus. A valve-like mechanism closes the opening in the shaft to prevent premature delivery of the composition during insertion of the shaft, and to prevent loss of composition during withdrawal of the shaft. The valve-like mechanism also prevents excessive delivery of the composition to targeted tissue. An annular dam is mounted on an exterior portion of the shaft near the opening. When the opening in the shaft has been suitably positioned in the targeted tissue, the dam is radially expanded to prevent quantities of composition intended for delivery to the targeted tissue from flowing away from the targeted tissue along the track though which the shaft is inserted.

30 Claims, 5 Drawing Sheets

APPARATUS FOR PREVENTING LOSS OF A COMPOSITION DURING A MEDICAL PROCEDURE

This application claims priority under 35 U.S.C. §119 based on provisional application Ser. No. 60/074,544, filed Feb. 12, 1998 and provisional application Ser. No. 60/056,836, filed Aug. 22, 1997, which are both hereby incorporated by reference herein in their entireties.

BACKGROUND OF THE INVENTION

The present invention pertains to instruments and methods for use in delivery of compositions, such as therapeutic fluids, through a tissue while minimizing exposure of the tissue to the compositions. More particularly, the invention pertains to treatment of a targeted tissue within an area of healthy tissue, and more particularly, to a multi-body apparatus and method capable of delivering compositions to a target tissue mass, such as, for example, a tumor, in the otherwise healthy tissue of a body organ, with minimum loss or exposure of the composition to the healthy tissue. The invention is particularly directed to multi-body apparatus capable of delivering compositions to a target tissue, such as brain tumor, while minimizing or preventing the exposure of healthy brain tissue to compositions that could potentially harm the healthy tissue.

DESCRIPTION OF THE PRIOR ART

In a method of treating a target tissue, such as, for example, a tumor, located within an otherwise healthy body organ, a composition in the form of a chemical, a therapeutic fluid, a dye, a contrast agent, a drug or a "cocktail" of chemicals, compositions and/or drugs, is delivered directly to the target tissue by injection.

Although this method is well suited for injection of fluid compositions, it will be understood by those skilled in the art that other compositions, such as, for example, viscous compounds, semi-fluids, or solids in granular or powdered form may also be injectable. Furthermore, the compositions may be injected in a liquid state and, after injection, solidify under the influence of body heat or by the application of an external energy source, such as, for example, microwave, radio frequency or electromagnetic energy. Alternatively, a solid or semisolid composition may be injected, and, after injection, liquify under the influence of body heat or an external energy source.

In this treatment method, after the location of the target tissue in an organ has been determined by MRI or other mapping or imaging method, a treatment apparatus having, for example, a needle or cannula capable of transporting a composition preferably in a fluid or semi-fluid state and having an opening at or near the tip for delivering fluid, is passed through healthy organ tissue until the tip opening is located within the tissue targeted for treatment, e.g. a tumor. A composition for treating the target tissue is transported from a reservoir at a proximal end of the treatment apparatus, through a needle shaft, and out through an opening at the distal tip of the needle. The fluid is delivered directly into the target tissue. This method has the advantage of localizing the treatment by specifically targeting tissue mass to be treated and is extremely successful in delivering the majority of the transported composition to the targeted tissue. The injection method is far less invasive than more radical treatments, such as, for example, surgery to remove tumor tissue, which can damage large amounts of healthy tissue. It also has advantages over traditional chemotherapy and radiology, which expose significant amounts of healthy tissue to side effects and possible damage.

This method of delivering a composition to a targeted tissue mass is particularly effective in treating brain tumors, since brain tissue is especially sensitive and susceptible to damage. For this reason, in the case of brain tissue treatment, needles are used which have a closed, rounded tip to minimize damage to healthy tissue and to prevent tissue from "packing" in the needle end. It will be understood by those skilled in the art that a variety of tips are also suitable, such as, for example, open tips, or pointed needle tips which are not "cutting" tips, etc. In addition to the particularly sensitive nature of brain tissue, certain types of brain tumors are known to have a high incidence of regrowth or recurrence. Patients with regrowing or recurring brain tumors may require multiple therapeutic treatments in the same location in the brain and, it is therefore desirable to keep to a minimum cumulative damage by multiple treatments. Thus, therapies for brain treatments in general need to be minimally damaging to healthy brain tissue.

Although the method of directly injecting fluids has been shown to be effective in specifically targeting and treating tissues, particularly in the brain, certain drawbacks are known. Compositions that are best suited to destroy tumor tissue are also known to negatively effect and possibly damage healthy tissue. And, although the method delivers the majority of the composition to the targeted tissue, some fluid may escape the shaft opening near the tip prematurely as it is being transported through healthy tissue to be located in the targeted tissue mass. Also, if the composition is injected under pressure into the target tissue, the fluid may not be absorbed quickly enough by the target tissue. If the fluid is not absorbed in the target tissue as quickly as it is injected, the fluid will seek a path of least resistance to escape the area of injection. The fluid may flow back along a track in the tissue. The track may be a pre-existing track in the tissue made by, for example, a diagnostic or other surgical instrument, or the track may be made by the treatment apparatus passing through the tissue. Alternatively, the track may be a naturally occurring lumen in the tissue, such as, for example, a vascular lumen, or may comprise an element of a guiding or positioning apparatus or device through which the treatment apparatus passes to reach the target tissue. The tendency for compositions to flow back along a track in the tissue, either while the treatment apparatus is in place or after the apparatus is withdrawn, will hereinafter be designated as "flow-back" or, alternatively, "retro-grade flow". In the case of either premature escape of fluid or flow-back of fluid, the effects are the same: healthy tissue is exposed to composition and may be damaged, and doses of composition intended for treating the target tissue may fail to be absorbed by or delivered to the target tissue. The problems of premature escape and flow-back are amplified by the fact that some of the most desirable compositions are low viscosity liquids with low surface tension characteristics. Due to their low viscosity, these fluids are highly likely to leak from the apparatus prematurely and/or flow back along the track to effect healthy tissue.

In view of the above-identified advantages and disadvantages, the present invention is directed to an apparatus and injection method for minimizing the adverse effects of compositions on healthy tissue in the tracks of surgical devices by minimizing or preventing premature escape and migration or flow-back of compositions during treatment

OBJECTS OF THE INVENTION

It is an object of the invention to provide a device and a method for treating target tissues, particularly brain tumors, by injecting a composition into the target tissue.

It is another object of the invention to provide a device and method for treating target tissues by injecting a composition while minimizing damage to healthy tissue caused by exposure to the composition.

It is another object of the invention to provide a multiple shaft apparatus capable of delivering composition to a target tissue without prematurely leaking the fluid onto the tissue of a patient or other person.

It is another object of the invention to provide a multiple shaft device with means capable of preventing premature escape of a composition.

It is another object of the invention to provide an injection device with a means to prevent flow-back of composition along an apparatus track.

It is another object of the invention to prevent flow-back of a composition so that the composition is more effectively delivered to the targeted tissue.

It is another object of the invention to prevent composition delivered to a target tissue from flowing back into the apparatus by providing a means of sealing the composition out of the apparatus to ensure full delivery to the target tissue.

The present invention is generally characterized in an apparatus with a body having multiple hollow coaxial shafts arranged to control the flow of compositions to a target. An inner shaft delivers a composition through a lumen extending from a reservoir at a proximal end of the inner shaft to an outwardly directed inner shaft opening near the distal end, or tip, of the inner shaft. A central shaft supports a flow control means in the form of a sleeve which is repositionable to selectively open and close the inner shaft opening. An outer shaft has an elastic portion on the distal end which can be temporarily radially expanded to form a dam to prevent fluid flow-back along the apparatus track.

These and further objects and advantages of the invention will become apparent from the following description of the preferred embodiment taken in conjunction with the accompanying drawings wherein identical reference numbers indicate identical parts or parts providing identical functions.

DETAILED DESCRIPTION OF THE INVENTION

Figures 1, 2:
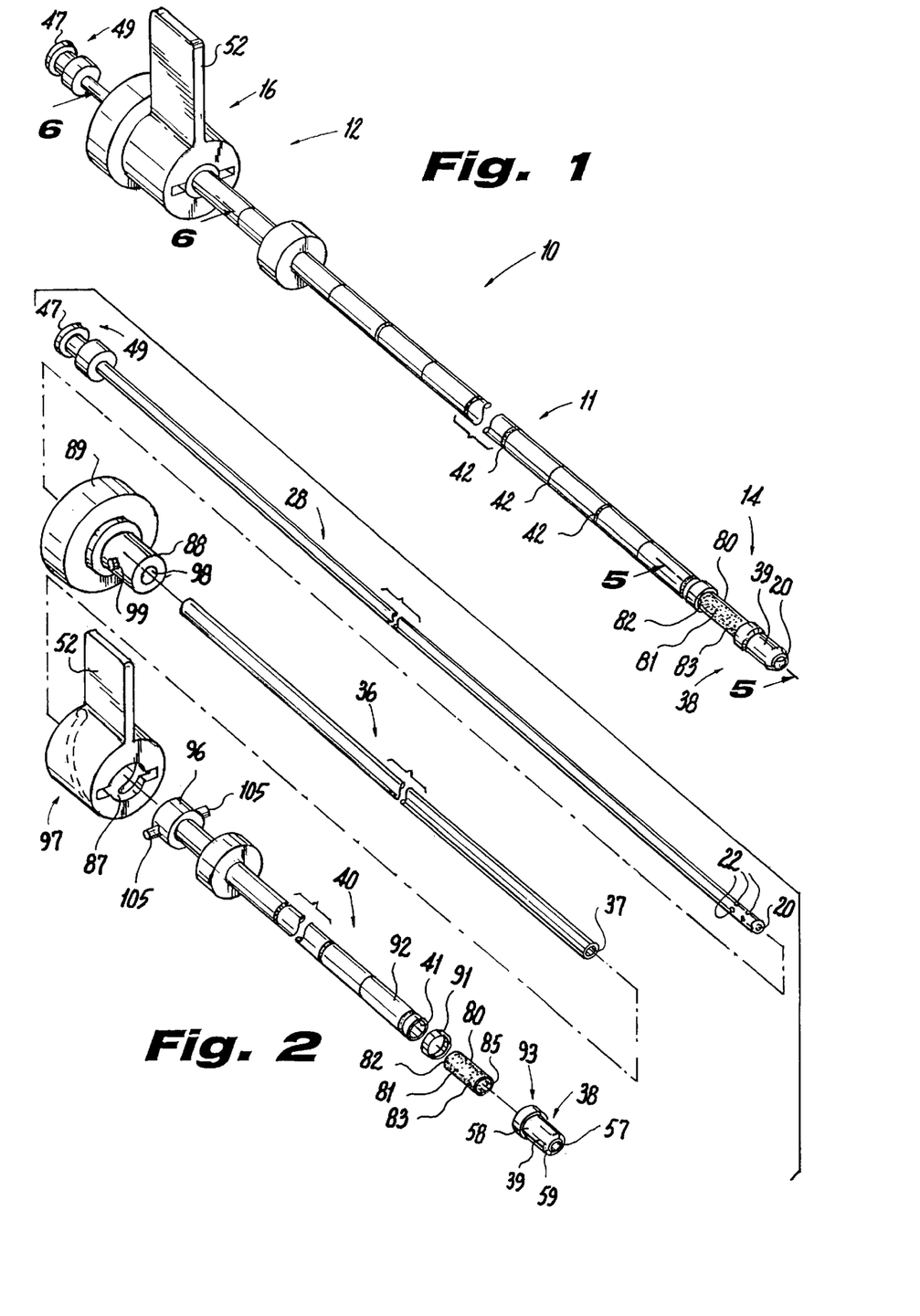
FIG. 1 is a perspective view of an apparatus according to the present invention with the valve closing the tip opening and the flow-back dam in an unexpanded state.
FIG. 2 is an exploded view of the apparatus according to the present invention showing the three shafts that make up the body of the apparatus.

Referring now to FIG. 1, an apparatus 10 is shown having a midsection 11 separating opposite proximal and distal ends 12, 14 respectively, and having a longitudinal axis along the length of the body from the proximal to the distal end. The body 10 has a control means 16 at the proximal end 12. The distal end 14 of the apparatus 10 may be steerable by conventional means, such as, for example, by providing a tip having a predetermined curved shape, or by providing a tip having a memory metal, such as nitinol. The preferred embodiment shown is intended for treatment of brain tumors, however, the inventor conteare addressed below.

The body 10 is comprised of three hollow shafts, as shown in FIG. 2, an inner shaft 28, an central shaft 36 and outer shaft 40, coaxially arranged along the longitudinal axis of the body 10 with each individual shaft having a tubular midsection and having proximal and distal ends substantially corresponding to the tubular midsection 11 and proximal and distal ends 12, 14, respectively, of body 10. The hollow shafts are preferably fabricated by known techniques from a surgical quality material, such as, for example, type 304 stainless steel with a full hard temper. The use of other materials to fabricate the shafts is also contemplated. For example, other surgical grade metals may be used, or polymer materials suitable for surgical applications may be used to fabricate the hollow shafts. Type 304 stainless steel is preferred as it is a well known material for similar applications, and is readily available for fabrication in the forms required. Type 304 stainless steel has the required strength, toughness and elasticity modulus to allow it to function properly with stereotactic frames such as those used in practicing the present invention. And type 304 stainless steel is known to be compatible with at least some of the compositions intended for use in this invention.

The outside diameters of the body could range in size, for example, from 10 mm for use in laparoscopy, to 0.2 mm for micro-procedures. The length, depending on the location of the target tissue from the body surface, could be in the range, for example, of from 50 cm for laparoscopy to 2 cm for other procedures. In the nominal preferred embodiment, i.e. the apparatus for treating brain tissue, outside diameter for each shaft is: an inner shaft 28 having a diameter of 1.07 mm, a central shaft 36 having a diameter of 1.47 mm, and an outer shaft having a diameter of 1.83 mm. The suggested length of the preferred embodiment will be approximately 30 cm.

Figure 3:
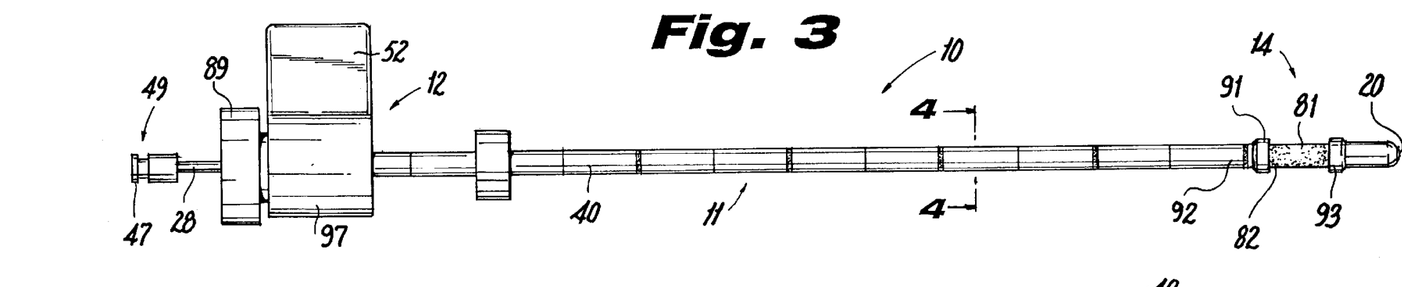
FIG. 3 is a side elevation view of the apparatus of the present invention with the valve at the apparatus tip closed and the flow-back dam retracted.
Figures 4, 5, 12:
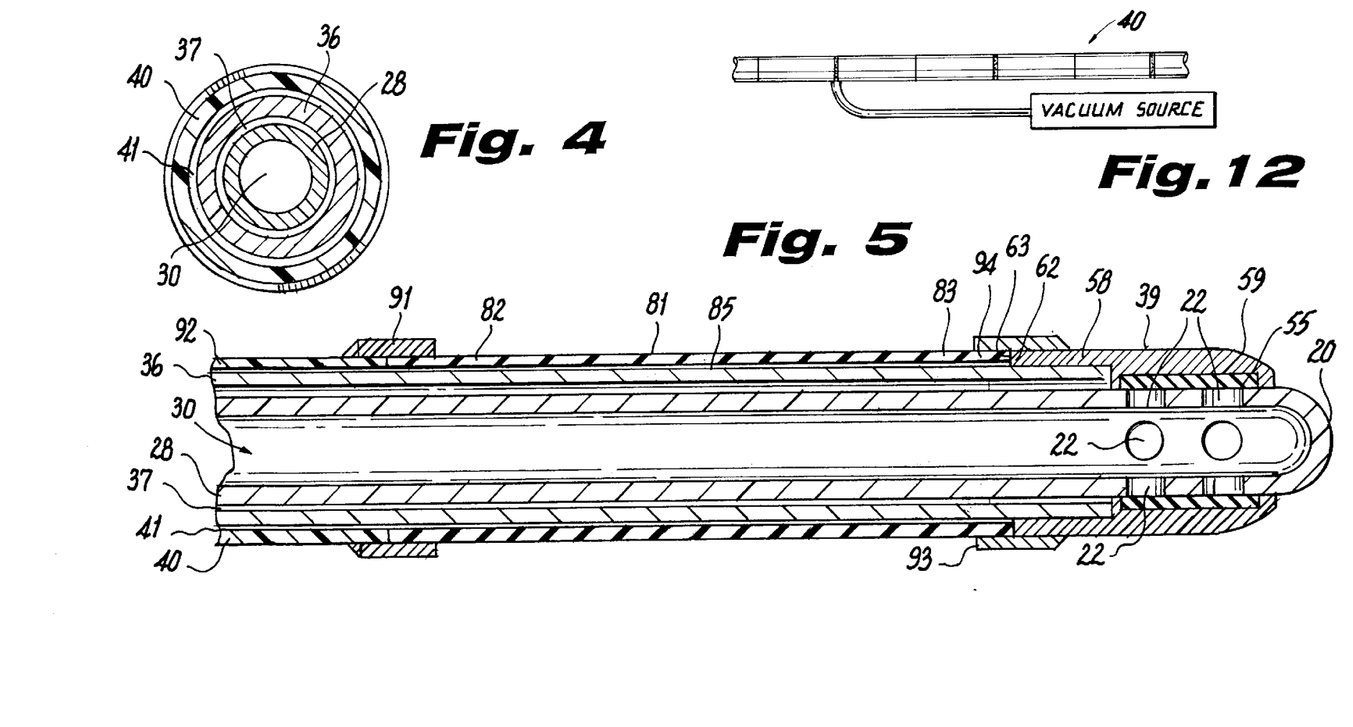
FIG. 4 is a cross-section view take along sectional line 4—4 in FIG. 3.
FIG. 5 is a cross-sectional view of the distal tip of the apparatus taken along sectional line 5—5 in FIG. 1.
FIG. 12 is a schematic diagram of another embodiment of the present invention.
Figure 6:
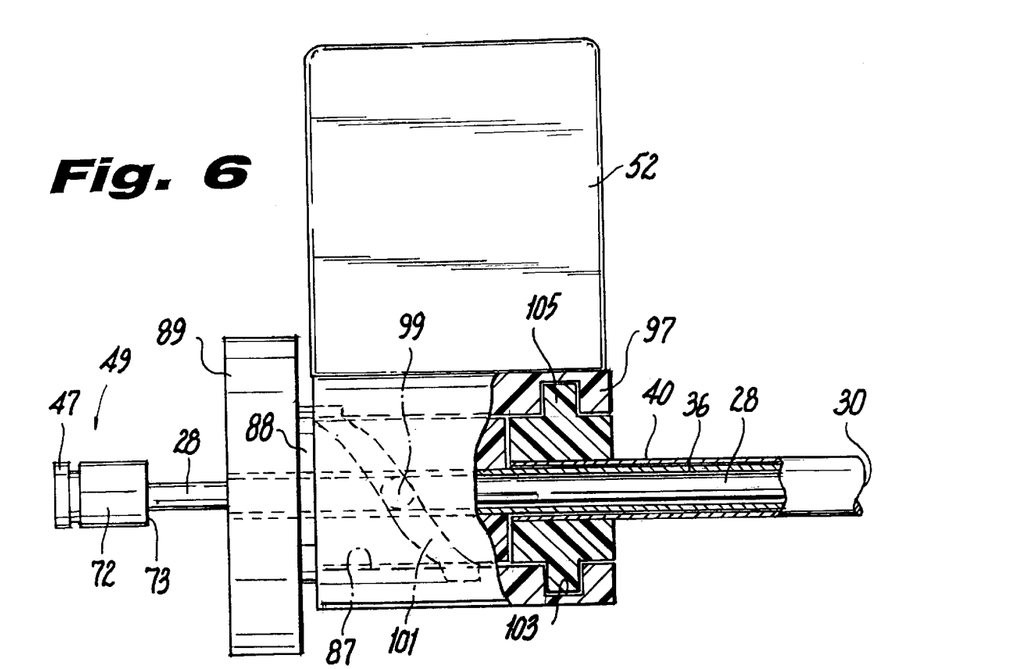
FIG. 6 is a partial cross-sectional view of the control means of the apparatus of the present invention in a first position.
Figure 7:
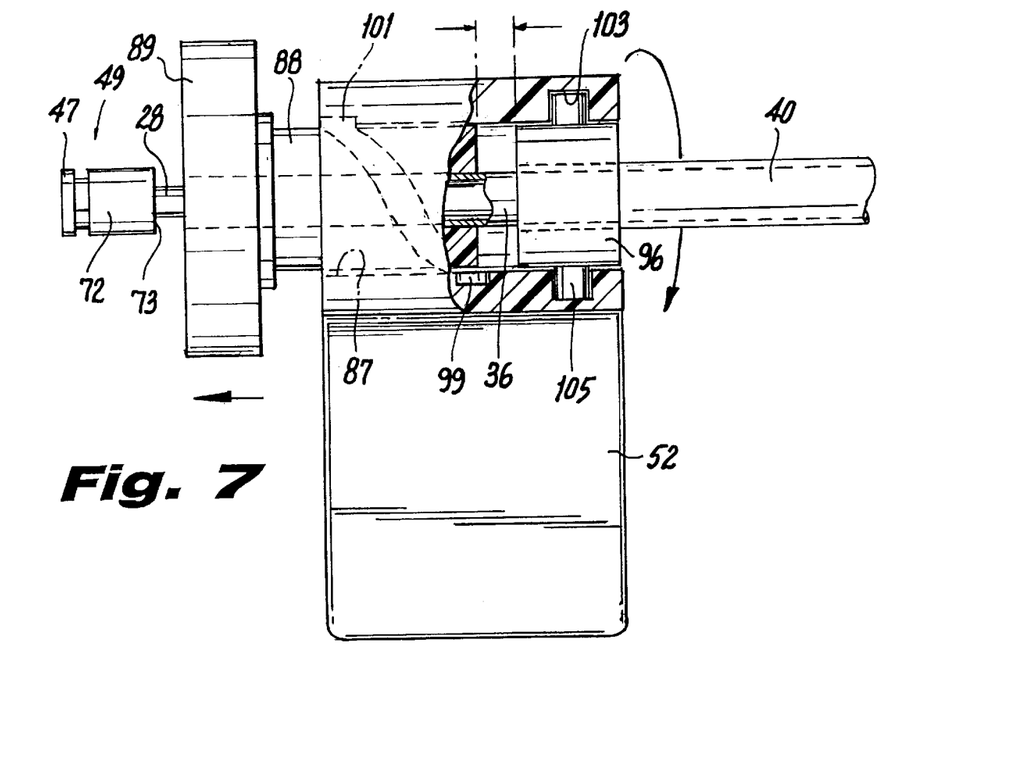
FIG. 7 is a partial cross-sectional view of the control means of the apparatus in a second position.
Figures 8, 9:
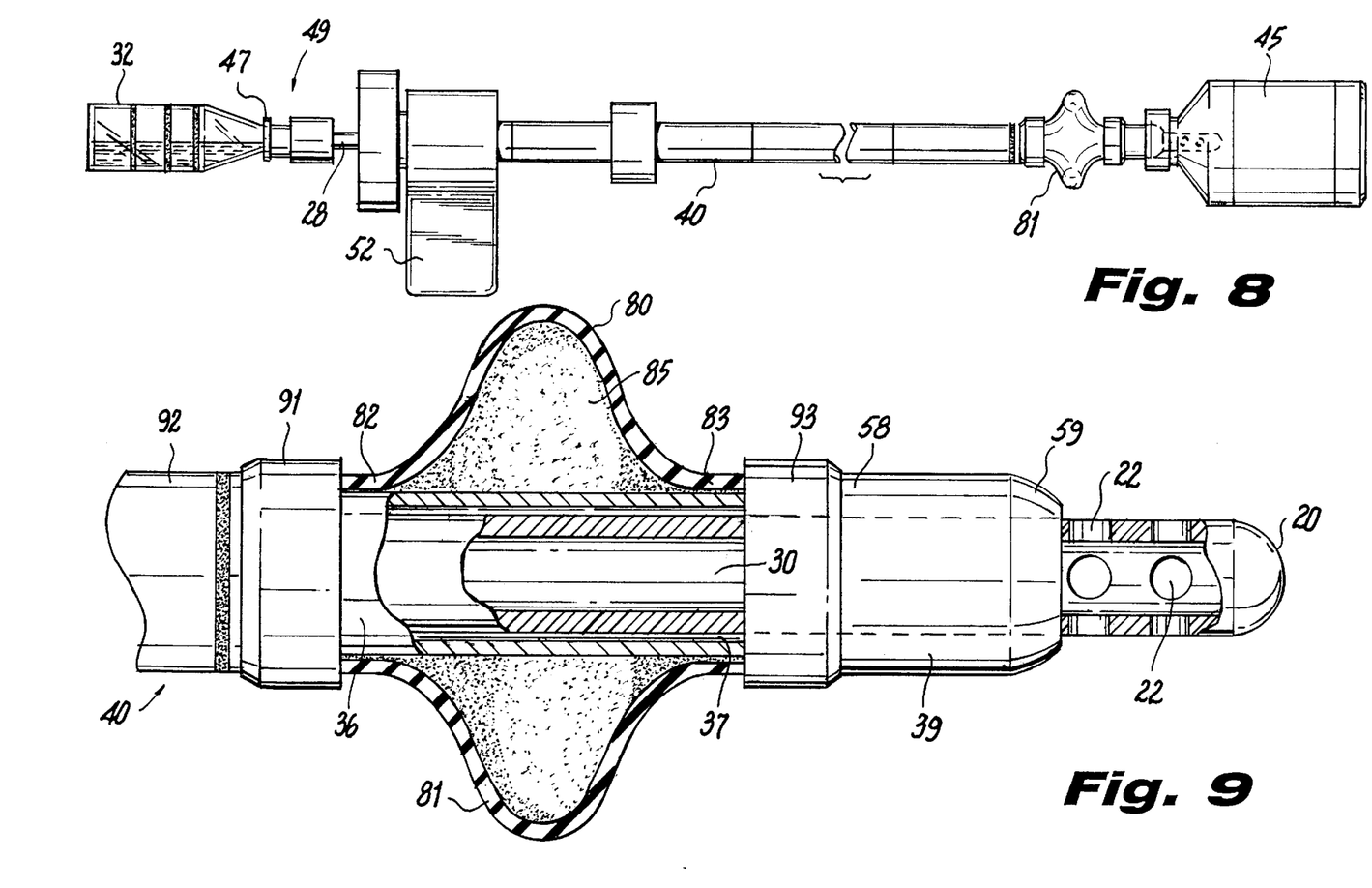
FIG. 8 is a side elevation view of the apparatus in use in a fluid supply mode.
FIG. 9 is a cross-sectional view the expanded dam.

The inner shaft 28 has a central, longitudinally oriented lumen 30, shown in FIGS. 4 and 5, which opens to a terminal fixture 49, shown in FIGS. 1–3, at the proximal end of the inner shaft 28. The terminal fixture 49 supports a connector means 47, such as, for example, a Luer connector, for attaching a fluid reservoir 32 (FIG. 8). The inner shaft lumen 30 opens at the distal end 14 of the body 10 to a tip opening 22 proximal to a tip 20 of the shaft. In a fluid supply mode, the lumen 30 serves as a conduit for compositions from tip opening 22 to the reservoir 32. For the purposes of this supply operation, the tip 20 and shaft tip opening 22 are temporarily immersed in an external fluid supply source such as, for example, bottle 45 (FIG. 8). Negative pressure is provided in reservoir 32 causing the composition to travel from the external fluid supply 45 through the tip opening 22, up through the conduit and into the reservoir 32. In a fluid delivery mode, the process is reversed, and lumen 30 serves as a conduit to transport compositions from the reservoir 32, which is provided with positive pressure during in the delivery mode, to the tip opening 22 at the distal end 14 of the body 10 for delivery through the tip opening 22 to the targeted tissue. Positive or negative pressure may be selectively provided to the reservoir 32 by a barrel and plunger (not shown) of conventional design, such as, for example, those found in a conventional syringe device, or by other known means for fluid delivery, in communication with the composition reservoir 32.

The preferred embodiment of the present invention is intended for treatment of tissue located in brain tissue. In treatments involving insertions through brain tissue, the tip 20 is preferably closed and blunt or rounded, to prevent excessive damage to the tissue and to prevent the brain tissue from blocking or plugging the tip opening 22 as it is being inserted. Alternatively, a pointed, "non-cutting" type tip may be used. In the preferred configuration, multiple tip openings 22 are located proximal to the tip 20 on a sidewall of the inner shaft 28, so that each opening 22 is oriented in a radially outwardly facing direction relative to the longitudinal axis of the body. Although the preferred embodiment is for treatment of brain tissue, and has a tip arrangement with a blunt, closed tip and a side oriented tip opening, the inventor contemplates the use of this invention for delivering compositions to target tissue in other organs, such as, for example, the liver. Thus, tip configurations suitable for a variety of tissue conditions and medical procedures are contemplated, including, for example, a conventional open pointed "cutting" tip suitable for treatment of other organs.

The inner shaft 28 is slidably supported in a complimentarily sized lumen 37 centrally located along the longitudinal axis extending from the proximal to the distal end of central shaft 36. Preferably, the outer dimension of the inner shaft 28 and the inner dimension of the lumen 37 of the central shaft 36 are sufficiently close to inhibit leakage of fluids between the shafts, while permitting the inner shaft to slide freely with respect to the central shaft. Alternatively, a seal or seals, such as, for example, an O-ring, a gasket, or a sealing material or compound may be provided to inhibit fluid leakage between the inner shaft and the central shaft. Similarly, a seal or seals are provided where necessary to other elements of the apparatus to prevent undesired flow of liquids between elements.

The inner shaft 28 has a length longer than central shaft 36 so that the proximal and distal ends of the inner shaft 28 can extend beyond the corresponding proximal and distal ends of central shaft 36 by a prescribed distance. The central shaft 36 is selectively repositionable to a limited degree relative to the inner shaft 28, thus the distance of extension of the inner shaft 28 with respect to the central shaft 36 can be manipulated. A push paddle 52 mounted on the proximal end of the central shaft 36 provides a means for manipulating the central shaft 36 with respect to the inner shaft 28 and the outer shaft 40.

A valve means 38 in the form of a sleeve 39 is securely mounted on the extreme distal end of central shaft 36 as an extension of the tubular form of shaft 36, so that the sleeve 39 is positioned coaxially about a portion of the distal end of the inner shaft 28. The sleeve 39 has a proximal end 58, a distal end 59 and a lumen 57. For reasons discussed below, the proximal end 58 of the sleeve 39 is provided with an outer diameter larger than the diameter of the central shaft 36 to which it is secured, thus forming an annular shoulder 62 with a bearing surface 63 directed towards the proximal end 12 of the body 10. Preferably, the outer diameter of the sleeve 39 is substantially similar to the outer diameter of the outer shaft 40, so that the outer surface of the body 10 is provided with a substantially smooth, obstruction free finish to facilitate the passage of the body through tissue during insertion and withdrawal operations. Between the proximal end 58 and the distal end 59, the outside diameter of the sleeve 39 is preferably reduced to provide a suitable taper from the full outside diameter of the outer shaft 40 to the outside diameter of the inner shaft 28. Thus, the tapered distal end 59 of sleeve 39 forms a smooth transition between the inner shaft 28 and the outer shaft 40 to facilitate insertion of the body 10 through tissue.

The diameter of the lumen 57 of the sleeve 39 is preferably the same as or slightly smaller than the diameter of the lumen 37 of the central shaft 36 so that the sleeve closely fits the circumference of the inner shaft 28 to form a slidable sealing engagement with the outer surface of the inner shaft 28. The sleeve 39 is selectively repositionable on the inner shaft 28 along the longitudinal axis of the body 10 by longitudinal movement of the central shaft 36. By moving the sleeve 39 longitudinally to its most distal position, about the portion of inner shaft tip 20 having the tip opening 22, the inner shaft tip opening 22 is sealed and compositions are prevented from leaking from the opening 22. By withdrawing the sleeve 39 longitudinally to a position proximal of the portion of the tip 20 having the tip opening 22, the tip opening 22 is exposed, and composition is permitted to pass freely through it.

Alternatively, the sleeve 39 can be provided with an aperture (not shown) which in a first radial position aligns with the tip opening 22 to permit fluids to pass, and which in a second position is radially offset from the tip opening 22, thereby blocking the tip opening 22 to prevent fluids from passing. Thus, the valve means may be selectively manipulated by radial movement of the central shaft 36 with respect to the inner shaft 28. In this embodiment, radial movement of the central shaft is selectively controlled by the push paddle 52 or some other suitable means.

Alternatively, the valve means 38 could comprise a valve, such as, for example, a one-way flapper valve (not shown) or elastic "aortic" type valve (not shown) at the tip 20 of the body 10.

The sleeve 39 may be made from any material which is capable of providing: a slidable sealing relationship with the inner shaft 28; a bearing surface, such as, for example, surface 63 on the shoulder 62, capable of supporting the forces necessary to expand dam 81; and, a secure attachment to the supporting central shaft 36. Metal, such as, for example, stainless steel, or polymer materials, such as, for example, Delrin or Polypropylene are suitable materials which can be fabricated to provide the proper sealing relationship with the inner shaft 28 and which can form a bearing surface capable of supporting the forces necessary to expand dam 81. The sleeve formed from such materials can be bonded or adhered to a stainless steel or polymer shaft body with a suitable adhesive, a suitable welding process, or another suitable mechanical fastening means, such as, for example, and annular ring or a swaged shaft end, etc. Polymer materials have the advantage of being capable of being formed in place, about the shaft body, by molding with suitable structural anchors, such as, for example, tabs, clearances, annular rings, swaging or grooves, provided on the shaft to secure the molded sleeve on the shaft. Polymer materials also have the advantage of providing, depending on formulation of the polymer, a better sealing capability and the flexibility to close the distal end of lumen 37.

Alternatively, if the shaft and seal are formed of the same material, they could be formed as one integral unit.

In the preferred embodiment, the sleeve 39 is fabricated from stainless steel. Stainless steel has the advantage of providing excellent fabrication qualities, structural integrity and, for the purpose of attachment to a supporting shaft, extremely secure mounting options, such as, for example, welding, swaging, threading or bonding to the body 10. Preferably, the ability of a stainless steel sleeve 39 to form a tight seal may be enhanced by providing a gasket 55 (FIG. 5) between the inner surface of the sleeve 39 and the outer surface of the inner shaft 28.

The sleeve 39 may have a uniform lumen diameter through the length of the sleeve. Providing the sleeve with a uniform lumen diameter would be required if the sleeve were fabricated from metal. However, a sleeve 39 fabricated from a polymer or other similar material could be provided with elastic qualities capable of conforming, at least at the distal end 59, to the shape of the inner shaft 28 as it curves to a rounded tip 20. Furthermore, enough elasticity could be provided to the distal end 59 of the sleeve 39 so that the distal end 59 would substantially close the sleeve lumen 37 completely, as shown in FIG. 1. Such a closure would be necessary in the case of an apparatus having an open, cutting tip instead of the rounded tip 20 and side opening 22 of the preferred embodiment shown in FIGS. 1–6.

The outer shaft 40 has a lumen 41 extending from the proximal to the distal end and sized to support in slidable engagement the central shaft 36. Preferably, the outer dimension of the central shaft 36 and the inner dimension of the lumen 41 of the outer shaft 40 are sufficiently close to inhibit leakage of fluids between the shafts, while permitting the central shaft to slide freely with respect to the outer shaft. Alternatively, a seal or seals, such as, for example, an O-ring, a gasket or a sealing material or compound, may be provided to inhibit fluid leakage between the central shaft and the outer shaft.

The outer shaft 40 may have calibration marks 42 on its outer surface suitable for use with gaging instruments such as, for example, a stereotactic or other type of locator frame for use with MRI or other imaging means. A radially expandable dam 81 comprised of an elastic portion 80 is provided on the distal end of the outer shaft 40 to selectively prevent fluid flow-back along the track. The dam 81 has proximal and distal ends, 82 and 83 respectively, and a lumen 85 substantially corresponding in diameter to the outer diameter of the central shaft 36. The dam 81 is positioned coaxially about a portion of the distal end of the central shaft 36, and may "free-float" in this position about the central shaft 36 while "captured" between a distally directed surface of the distal end of the outer shaft 40 and the proximally directed bearing surface 63 of the sleeve 39. Alternatively, the proximal end 82 of the dam 81 may be fixedly mounted on the distal end of outer shaft 40 as an extension of the tubular form of shaft 40 while the distal end 83 of the dam 81 engages but is not fixedly attached to the bearing surface 63 of the sleeve 39. Alternatively, the distal end 83 of the dam 81 may be fixedly mounted on the bearing surface 63 of the sleeve 39, while the proximal end 82 of the dam 81 engages but is not fixedly attached to the distal end of the outer shaft 40. Alternatively, the dam 81 may be fixedly mounted on both the proximal and distal ends, 82 and 83 respectively. The secure attachment may be made by any known means, including but not limited to the mounting methods mentioned above. In the preferred embodiment, the proximal end 82 of the dam 81 is fastened to the distal end of the outer shaft 40 by an annular steel band 91 or swaged outer shaft end 92. Preferably, the distal end 83 of dam 81 engages but is not secured to bearing surface 63 of shoulder 62 on the sleeve 39. An annular steel band 93, secured to the outer surface of the proximal end of the sleeve 39 such that the proximal end of the steel band 93 extends proximally beyond the proximal end of the sleeve 39, forms an annular groove 94 in which the distal end 83 of the dam 81 is seated. The steel band 93 is preferably not secured to the distal end 83 of the dam 81. The annular groove 94 formed by the steel band 93 prevents the unsecured distal end 83 of the dam 81 from riding up over the proximal end of the sleeve 39 when, as explained in more detail below, the bearing surface 63 engages the distal end 83 of the dam 81 to expand the dam.

The dam 81 is fabricated from an elastic material or materials suitable for surgical applications, such as, for example, a silicone or rubber elastomer. In a unexpanded position, the dam 81 has a uniform outer diameter substantially equal to the outer diameter of the outer shaft 40. With the dam 81 in the unexpanded state, the body 10 carrying the dam 81 on outer shaft 40 can be readily inserted or withdrawn through healthy tissue to the tissue targeted for treatment. The dam 81 can be radially expanded by the longitudinal movement of the central shaft 36 with respect to the outer shaft 40 such that the bearing surface 63 on shoulder 62 of the sleeve 39, bearing against the distal end 83 of the dam 81, compresses the distance between the proximal end 82 and distal end 83 of the dam 81, thus forcing the soft elastic portion 80 of the dam to expand radially outwardly.

Although in the preferred embodiment, the dam 81 in a unexpanded position has an outer diameter substantially equal to the outer diameter of the outer shaft 40, it will be understood that the dam could also be constructed so that the elastic portion 80 is biased toward the radially expanded position, so that in the "unexpanded" state, the outer diameter of the dam 81 is substantially greater than the outer diameter of the outer shaft 40. This construction would require the fixed attachment of the proximal end 82 of the dam 81 to the distal end of the shaft 40 and the fixed attachment of the distal end 82 of the dam 81 to the proximal end 58 of the sleeve 39. The radially expanded position of the dam 81 could then be radially reduced to substantially the same outer diameter as the outer shaft 40 by longitudinal movement of the central shaft 36 relative to the outer shaft 40 such that the distance between the distal end of the outer shaft 40 and the proximal end 59 of the sleeve 39 is increased, thus forcing the elastic portion 80 to stretch and be reduced in diameter.

Alternatively, rather than simply expanding radially outwardly, the dam could be engineered such that compressing the distance between the ends of the dam 81 would cause the walls of the dam to fold back on themselves, the overlapping walls thereby providing an annular expanded portion about the body.

Alternatively, the dam 81 could have proximal and distal ends 82 and 83 respectively, fixed in a sealed relationship with the outer shaft and the central shaft such that fluid pressure provided to the lumen of the outer shaft would inflate and expand the dam. In another alternative embodiment, the dam could take the form of a passive plug. The outer shaft would have a portion near the tip with a permanent bulge biased radially outwardly only with sufficient bias so that the bulge is naturally compressed by the tissue during insertion and withdrawal of the apparatus body 10. When the body 10 is stationary, however, the "passive-plug" would automatically expand to prevent flow-back.

In another alternative embodiment, substantially the entire length of the outer shaft which is located in the apparatus track comprises a dam made of a elastic material. The elastic wall outer shaft can be inflated by fluid pressure provided to the lumen of the outer shaft. In this embodiment, substantially the entire apparatus track would be sealed by engagement with the inflated elastic outer shaft.

In yet another embodiment, the entire outer shaft comprises an elastic material which is expanded by inserting an apparatus tube of a dimension slightly larger that the apparatus track dimension (disclosed in another context in U.S. Pat. No. 5,454,790).

As a means for inhibiting a migration of the composition along the track, the dam 81 creates a seal at an interface of the apparatus 10 and the track through which the apparatus 10 is inserted. In order for the seal to effectively inhibit the flow of composition between the apparatus 10 and the track, the seal must exert a pressure between the apparatus and the track which is equal to or greater than the pressure at which the composition is delivered through the tip of the apparatus into the target tissue. In the preferred embodiment, this pressure is provided by the outwardly expanding dam 81. A similar sealing pressure between the track and the apparatus 10 can be provided by pulling the track against the apparatus 10. This can be accomplished by providing sufficient negative pressure, or vacuum, to the surface of the apparatus outer tube. By way of the vacuum, the track will be drawn tightly into sealing engagement with the apparatus body to prevent flow-back of composition from the target tissue.

As an alternative means for inhibiting a migration of the composition along the track, a portion of the external surface of the apparatus which is in contact with the track can be mechanically or chemically altered to adhere to the track. For example, the surface tension of the apparatus surface or the track surface can be modified to enhance adhesion of the track surface to the apparatus surface, and thus inhibit a migration of the composition along the track.

Inner shaft 28 is preferably free relative to both the outer shaft 40 and central shaft 36. The inner shaft 28 may thus be completely withdrawn from within the central shaft for exchange, maintenance or replacement during a therapeutic procedure.

A control mechanism 16, preferably calibrated, located at the proximal end of the body 10 facilitates movement of the shafts with respect to each other. In the preferred embodiment, the outer shaft 40 and central shaft 36 are movably connected to one another by control mechanism 16. A collar-like ring 96 is rigidly secured to the proximal end of the outer shaft 40 by any suitable means, but preferably by screw threads. The proximal end of central shaft 36 passes through the collar-like ring 96, extending proximally from collar-like ring 96. A collar-like knob 89 with a central aperture 98 is rigidly secured onto the proximal end of central shaft 36 by any suitable means, but preferably by screw threads. The collar knob 89 has a distally directed reduced diameter portion 88. Inner shaft 28 is dimensioned to pass freely through the aperture 98. Push paddle 52 has a central collar 97 with an aperture 87 which extends from a proximal to a distal end of the push paddle collar. The aperture 87 is dimensioned on the proximal end to receive the reduced diameter portion 88 of collar knob 89. The push paddle 97 is movably supported on the reduced diameter portion 88 of knob collar 89. An outwardly projecting annular lug 99 secured in the aperture 87 of the push paddle collar 97 rides in a corresponding suitably dimensioned inwardly facing helical groove 101 on the reduced diameter portion 88 of the knob 89. The lug 99 serves to guide the movement of the central shaft 36 and outer shaft 40 with respect to each other. Similarly the aperture 87 of the push paddle collar 97 is dimensioned on a distal end of the push paddle collar 97 to receive and support the outer shaft collar 96. A suitably dimensioned outwardly projecting annular lug 105 secured on the outer shaft collar 96 of the outer shaft 40 engages an inwardly facing annular slot 103 located inside the distal end of the push paddle collar 97. Thus, the central shaft 36 is movably secured to the outer shaft 40 by way of the central shaft knob 98 connected to the push paddle collar 97, which in turn is movably connected to the outer shaft collar 96.

At least one of the respective slot and lug combinations has a slot with a pitch along its length which is capable of providing travel of 0.060 inch relative to the longitudinal axis of the apparatus shaft. This pitched slot translates the radial movement of the push paddle 52 to a longitudinal movement, or travel, of the central shaft 36. The pitch of the slot is calibrated to provide a predetermined longitudinal movement of the shaft corresponding to specific radial movement of the push paddle. For example, movement of the push paddle through 180 degrees results in 0.060 inch travel for the central shaft 36 relative to the outer shaft 40. In use, once the tip 20 has been located in the tissue to be treated, the outer shaft 40 is preferably fixed relative to the patient, or relative to the tissue being treated, by means of a stereotactic frame 195 (FIG. 10) or similar device. Movement of the central shaft 36 in a proximal direction relative to the outer shaft 40 along the longitudinal axis of the body 10 simultaneously opens the valve means 38 and expands the dam 81 at the distal end of the body 10. This longitudinal movement of the central shaft 36 is controlled by radial movement of the push paddle which can be connected to the central shaft 36 and the terminal fixture 49 in any suitable way such that the necessary movement of the central shaft can be effected.

Embodiments of the apparatus having one, two, three, or more shafts are contemplated by the inventors. For example, instead of an apparatus having three coaxial shafts with one shaft controlling the dam expansion, an apparatus could be constructed having only one or two shafts with a radially expanded annular dam separately mounted on an external surface of the apparatus, and with thin pieces of a flexible member (not shown), such as a steel wire, provided inside or outside the shaft(s) to control dam expansion. In a single shaft apparatus, the elastic tube comprising the annular dam 81 could function as the valve means and the dam. A proximal end of the elastic tube would be rigidly fixed to the outside of the single shaft apparatus near the distal end of the shaft, at a point between the aperture 22 and the proximal end of the shaft, by a steel band, a collar or other attachment means. The distal end of the dam comprising the dam would have a steel band or other suitable collar capable of movably mounting the distal end of the elastic tube in a sealing relationship on the outside of the shaft at a point between the aperture 22 and the tip 20. A steel wire attached at a first end to the band or collar of the distal end of the dam, and at an opposite end to the control means 16, would be used to draw the movable distal collar of the dam toward the fixed proximal attachment point of the dam, thus simultaneously exposing the aperture 22 and expanding the dam 81.

Alternatively, thin members, such as, for example, a steel wire, could be provided to push a proximal end of an elastic tube comprising a dam 81, which proximal end is movably mounted to a shaft, toward a distal end of the elastic tube which is fixedly mounted to the shaft, thus expanding the dam 81. Between the proximal and distal ends of the apparatus, the thin member could be positioned in an existing shaft lumen, or in a separate lumen dedicated to the thin member. Alternatively, the thin member could be positioned externally of the apparatus to run alongside the shaft in the apparatus track through the tissue. The thin member should be dimensioned to provide sufficient flexibility to permit the thin member to pass through the lumen of a shaft and possibly to bend sufficiently to pass through the shaft wall to connect to the elastic tube comprising the dam. The thin member would also be required to have rigidity sufficient to transmit the pushing force necessary to cause the expansion of the dam 81.

As noted above, the valve means 38 may comprise a sleeve 39 with at least one aperture which corresponds to the tip aperture 22. The corresponding sleeve aperture would be radially offset to inhibit flow of liquid from the aperture, and moved to a radially aligned position to expose the tip aperture 22 to permit the flow of fluid through the aperture. In this embodiment, the dam 81 could also be expanded by a the radial movement of at least one rotating member. For example, a cam mechanism could be provided inside the elastic tubing comprising the dam 81 to expand the dam. Rotation of a cam in the mechanism would cause expansion of the dam 81.

Terminal fixture 49 may have a shoulder 72 with a surface 73 facing the distal end 14 of the body 10, providing a reference for calculating the extension of inner shaft 28 from central shaft 36. In addition to providing an extension reference, the surface 73 of shoulder 72 provides a stop to prevent over extension of the inner shaft 28 beyond the end of central shaft 10.

In use, a target tissue must first be located and mapped in the brain by using MRI, or alternatively, computer tomography, ultrasound or other imaging method. The initial location and mapping of the target tissue and the subsequent manipulation of the apparatus of the present invention to direct it to the target tissue may be accomplished by any suitable targeting and/or manipulation apparatus, method or procedure including instruments or elements separate from or integral with the present apparatus. For example, tissue may be targeted and the apparatus guided by means of any energy source, such as, absorption, defraction, scatter, or radiation, including any energy spectra such as infrared, X-ray, or visible light, including CT (computed tomography), MRI (magnetic resonance imaging), PET (position emission tomography), SPECT (single position emission computed tomography), or ultrasound. Furthermore, tissue may be targeted and the apparatus of the invention manipulated through any instrumentation approach modality, such as, for example, a trocar for percutaneous procedures. The following are other examples of targeting and/or manipulation apparatus, methods or procedures, the principles of which may be applied, either alone or in combination, to any tumor or anatomical structure of interest:

1. Laparoscopic—e.g. for intra-abdominal injection of liver tumors, abdominal metastasis, or the delivery of agents to abdominal organs by direct injection through the use of laparoscopic instrumentation, with or without, for example, visualization by the use of a viewing wand or other viewing device.
2. Thoracoscopy—e.g. for the injection of lung tumors or pleural metastasis, through the use of thoracoscopic instrumentation, with or without, for example, visualization by the use of a viewing wand or other viewing device.
3. Percutaneous—e.g. the percutaneous injection of liver or other tumors using ultrasound guidance for needle positioning.
4. Stereotactic—e.g. the direct injection of a brain tumor, with or without a stereotactic frame, following tumor localization by MR imaging.
5. open cavity—e.g. the direct injection of a tissue or organ accessed by an open surgical procedure.
6. minimally invasive/microsurgical—e.g. use of the device with a neuro-endoscope and image guided surgery system such as Philip's EasyGuide™ Neuro.

The suggested apparatus, methods or procedures may require direct manipulation (by hand) or indirect manipulation, such as, for example:

1. mechanically aided—e.g. a fixed trajectory guidance device (Patel & Sandeman, Computer Aided Surgery, 1997, 2; 186–92, incorporated herein by reference).
2. robotically aided—e.g. a robotic laparoscope positioner (automated endoscope system for optimal positioning, a.k.a. AESOP), Computer Motion Inc.

Figure 10:
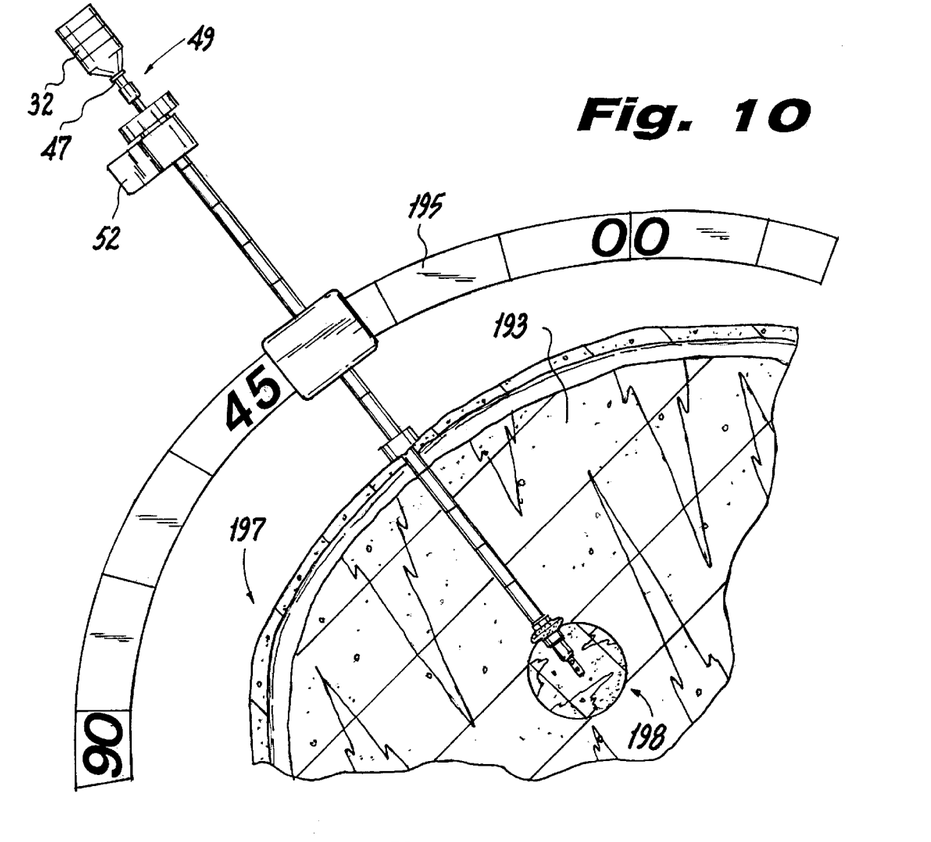
FIG. 10 is a view of the apparatus as used in conjunction with a stereotactic frame.
Figure 11:
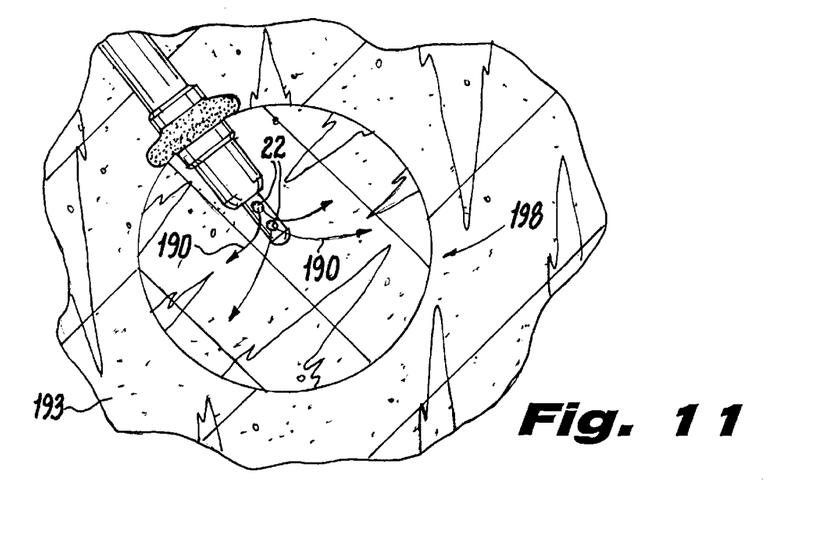
FIG. 11 is an enlarged view of the tip of the apparatus in a target tissue.

In a preferred embodiment, a suitable stereotactic frame 195 is secured to the head of the patient 197 and images are created. These images are used to determine the best approach for a biopsy instrument to enter the target tissue 198 and retrieve a biopsy specimen. The images are also used to determine the precise location and the best approach for the treatment. A biopsy is often performed using the stereotactic frame 195 to support and guide the biopsy instrument. The biopsy specimen is removed and confirmed. The stereotactic frame 195 used for the biopsy may also be used to support the apparatus 10 and guide the tip 20 to the proper location in the target tissue 198. The distal portion of the body 10 may be inserted through healthy tissue 193 to locate the tip 20 in a target tissue 198. Alternatively, the distal portion of the body 10 may be inserted directly into the target tissue 198, without the tip 20 or body 10 contacting healthy tissue, by passing the body 10 through a pre-prepared opening, such as, for example, a resection cavity. In either case, the valve means 38 of the present invention is expanded to prevent premature escape of composition which could potentially harm healthy tissue in a track created by the apparatus body 10 in healthy tissue or in healthy tissue exposed in a resection cavity. Furthermore, by preventing flow-back, either through a track in tissue or through a track in a guiding, targeting, position or manipulating device cooperating with the apparatus, the dam 81 assures that a maximum intended quantity of composition remains in the target tissue 198 until the composition has served its function by being absorbed or otherwise utilized.

When the tip 20 of the apparatus has been properly positioned in target tissue 198 to be treated, the inner shaft 28 and the outer shaft 40 are held stationary relative to the stereotactic frame, and thus, stationary relative to the target tissue 198, i.e., the tissue being treated. The retracted dam 81 is positioned approximately at the outer periphery of the target tissue 198. The central shaft 36 is then drawn longitudinally towards the proximal end 12 of the apparatus body 10 by radially rotating the push paddle 180 degrees. The sleeve 39, which is fixed to and moves with the central shaft 36, and which bears against the distal end 83 of the dam 81, moves towards the distal end of the outer shaft 40, thus compressing the distance between the distal end 83 and the proximal end 82 of the dam 81. Compression of the distance between the ends 82, 83 of the dam 81 causes the dam 81 to expand radially outwardly, and thus to exert pressure against the walls of the apparatus track thereby preventing flow-back of fluid along the apparatus track by sealing the apparatus track. As noted above, the apparatus track may be a track through tissue, created by the apparatus or another surgical instrument being forced through the tissue, or the apparatus track may be a track through an auxiliary surgical device, such as, for example, a lumen in a guiding, targeting, positioning or manipulating instrument in which the apparatus is cooperatively positioned to access the target tissue. A single apparatus track may also comprise a portion which passes through tissue and a portion which passes through an auxiliary surgical device. Thus, to prevent flow-back the radially outwardly expanded dam 81 may exert sealing pressure against tissue, i.e., in an apparatus track through tissue, or against the structure of an auxiliary surgical device, such as, for example, the inner walls of a lumen of an endoscopic, laproscopic or thoracospic instrument. Furthermore, where a single apparatus track passes through tissue and through an auxiliary surgical device, one or more dams 81 may be provided to seal both the portion passing through tissue and the portion passing through the auxiliary surgical device.

The components of the apparatus are preferably arranged so that when the central shaft 36 is moved longitudinally towards the proximal end of the body 10 relative to the outer shaft 40 to radially expand the dam 81, the central shaft 36 also moves relative to inner shaft 28. Longitudinal movement of the central shaft 36 relative to the inner shaft 28 causes the tip opening 22 to be exposed. Composition is then passed from the reservoir 33 through the lumen 30 of the inner shaft 28, and through the exposed tip opening 22 to the tissue to be treated. The composition flows out of the tip openings 22 in the direction of arrow 190, and because the dam 81 has been expanded at the periphery of the target tissue 198, composition is prevented from flowing back up the apparatus track in healthy tissue 193. The dam 81 is held in the expanded position to prevent flow-back for a period of time sufficient to permit the composition to be substantially absorbed or otherwise utilized in the target tissue. In addition to inhibiting flow-back of composition along the apparatus track, the dam serves to anchor and stabilize the body in the patient, thus preventing accidental withdrawal or hyper insertion of the body in a patient if the patient moves during the "holding" period of the treatment, e.g. while the dam is expanded so that composition can be absorbed by the tissue being treated. When the composition has been substantially absorbed or otherwise utilized in the target tissue 198, the central shaft 36 is moved toward the distal end of the body 10, which in turn moves the sleeve 39 to its position covering the tip openings 22, preventing further passage of fluid, and causing the dam 81 to unexpand and contract to its original unexpanded position. Covering, i.e., closing, the tip openings 22 not only prevents further passage of composition from the apparatus which could damage healthy tissue as the apparatus is withdrawn, but also prevents delivered compositions in the targeted tissue from flowing back into the apparatus. The apparatus body can then be safely withdrawn from the patient.

Inasmuch as the present invention is subject to many variations, modifications and changes in detail, it is intended that all subject matter discussed above or shown in the accompanying drawings be interpreted as illustrative only and not be taken in a limiting sense.

What we claimed is:

1. An apparatus for delivering a composition to a target area of a tissue, the apparatus traversing a track in the tissue, the apparatus comprising:

an elongate tubular inner member having a proximal end, a distal end and a lumen extending from the proximal end to the distal end of the inner member, said lumen adapted to receive a fluid at the proximal end of the inner member, and means for delivering said fluid from the distal end of the inner member to the target tissue by way of the lumen;

an elongate tubular central member having a proximal end, a distal end and a lumen extending from said central member proximal end to said central member distal end, said tubular inner member being coaxially positioned in said lumen of said central member;

an elongate tubular outer member having a proximal end, a distal end, lumen extending from said outer member proximal end to said outer member distal end, said tubular central member being coaxially located in said lumen of said outer member; and means for inhibiting a migration of said composition along the track from said target area comprising a selectively, radially expandable sleeve biased toward a radially expanded position when the apparatus is stationary in said tissue, is sufficiently radially compressible to permit movement of said apparatus in said tissue, wherein said radially expandable sleeve has a proximal end and a distal end, said proximal end and distal ends being restrained from expanding, and said proximal end and distal end are separated by an expandable portion having a predetermined length and wherein the proximal end of the sleeve is engaged by the distal end of the outer member and the distal end of the sleeve is engaged by the distal end of central member and, wherein movement of said central member relative to the outer member causes a reduction in a distance between said proximal and distal ends of said sleeve so that said expandable portion of said sleeve expands radially outward.

2. The apparatus according to claim 1 wherein the means for inhibiting a migration is adapted to selectively seal the composition in the apparatus as the apparatus is inserted through the track.

3. The apparatus according to claim 1 wherein the means for inhibiting a migration is adapted to selectively seal the composition in the apparatus while the apparatus is positioned in the tissue.

4. The apparatus according to claim 1 wherein the track is formed by the insertion of the apparatus into said tissue.

5. The apparatus according to claim 1 wherein said means for inhibiting a migration is located proximal to said means for delivering fluid.

6. The apparatus of claim 1 further comprising means for providing selective interruption of composition delivery to said target area.

7. The apparatus for delivering a composition to a target area of a tissue according to claim 1, wherein the means for delivering is stationary relative to the means for inhibiting migration of the composition along the track.

8. The apparatus according to claim 1 wherein the means for delivering is movable relative to the means for inhibiting a migration of said composition along the track from said target area.

9. The apparatus according to claim 1 wherein the distal end of the inner member is steerable.

10. The apparatus according to claim 1, where in the delivery means may be selectively positioned within the target area.

11. The apparatus according to claim 1, wherein the apparatus is introduced into the target tissue by surgical means.

12. The apparatus according to claim 1 further comprising imaging means for locating the target tissue.

13. The apparatus according to claim 1 wherein the radially expandable sleeve is a balloon.

14. The apparatus according to claim 13 wherein the balloon is expanded by mechanical means.

15. The apparatus according to claim 1, wherein said movement of said central member relative to said outer member is along a longitudinal axis of said apparatus.

16. The apparatus according to claim 1, wherein said distal end of said central member has a radially outwardly directed annular shoulder, said shoulder forming a proximally facing annular bearing surface, and wherein said distal end of said sleeve engages said bearing surface of said shoulder.

17. The apparatus according to claim 1, wherein the proximal end of the sleeve is secured to the distal end of the outer member, the distal end of the sleeve is engaged by the distal end of the central member, and wherein a longitudinal movement of the central member relative to the outer member in a direction to cause a reduction in the distance between the proximal and distal ends of the sleeve causes said expandable portion of sleeve to expand radially outwardly.

18. The apparatus according to claim 1, wherein the proximal end of the sleeve is secured to the distal end of the outer member, the distal end of the sleeve is engaged by the distal end of the central member, and wherein a longitudinal movement of the central member relative to the outer member to cause a reduction in the distance between the proximal and distal ends of the sleeve causes said expandable portion of sleeve to expand radially outwardly.

19. The apparatus according to claim 1, wherein said radially expandable sleeve is comprised of an elastic material.

20. An apparatus for delivering a composition to a target area of a tissue, the apparatus traversing a track in the tissue, the apparatus comprising:

an elongate tubular inner member having a proximal end, a distal end and a lumen extending from the proximal end to the distal end of the inner member, said lumen adapted to receive a fluid at the proximal end of the inner member, and means for delivering said fluid from the distal end of the inner member to the target tissue by way of the lumen;

an elongate tubular central member having a proximal end, a distal end and a lumen extending from said central member proximal end to said central member distal end, said tubular inner member being coaxially positioned in said lumen of said central member;

an elongate tubular outer member having a proximal end, a distal end, lumen extending from said outer member proximal end to said outer member distal end, said tubular central member being coaxially located in said lumen of said outer member; and means for inhibiting a migration of said composition along the track from said target area, wherein said means for inhibiting migration of said composition is a vacuum provided along a portion of the apparatus in the tissue such that an adjacent portion of tissue collapses onto the apparatus.

21. The apparatus of claim 20, wherein the track in said tissue from said target area is created by insertion of said apparatus.

22. The apparatus according to claim 20 wherein said means for inhibiting a migration is located proximal to said means for delivering fluid.

23. The apparatus of claim 20 further comprising means for providing selective interruption of composition delivery to said target area.

24. The apparatus according to claim 20, wherein the means for delivering is stationary relative to the means for inhibiting migration of the composition along the track.

25. The apparatus according to claim 20 wherein the means for delivering is movable relative to the means for inhibiting a migration of said composition along the track from said target area.

26. The apparatus according to claim 20 wherein the distal end of the inner member is steerable.

27. The apparatus according to claim 20, where in the delivery means may be selectively positioned within the target area.

28. The apparatus according to claim 20, wherein the apparatus is introduced into the target tissue by surgical means.

29. The apparatus according to claim 20 further comprising imaging means for locating the target tissue.

30. The apparatus of claim 1, wherein the means for delivering said fluid is axially movable relative to the means for inhibiting migration.

* * * * *

UNITED STATES PATENT AND TRADEMARK OFFICE
CERTIFICATE OF CORRECTION

PATENT NO. : 6,203,526 B1
DATED : March 20, 2001
INVENTOR(S) : McBeth et al.

It is certified that error appears in the above-identified patent and that said Letters Patent is hereby corrected as shown below:

Title page,
Item [75], Inventors, "Dean M. McBeth" should be -- Dean McBeth --.

Item [56],
References Cited, under the heading
U.S. PATENT DOCUMENTS, insert:

| | | | | |
|---|---|---|---|---|
| -- 3,938,530 | 2/1976 | Santomieri | 604 | 105 |
| 4,571,241 | 2/1986 | Christopher | 604 | 104 |
| 5,041,093 | 8/1991 | Chu | 604 | 104 -- |

Signed and Sealed this

Twentieth Day of November, 2001

Attest:

*Nicholas P. Godici*

NICHOLAS P. GODICI
*Attesting Officer*   *Acting Director of the United States Patent and Trademark Office*